United States Patent
Roundhill et al.

(10) Patent No.: US 6,602,194 B2
(45) Date of Patent: Aug. 5, 2003

(54) DUAL BEAMFORMER ULTRASOUND SYSTEM FOR 2D AND 3D IMAGING

(75) Inventors: David N. Roundhill, Woodinville, WA (US); Roy B. Peterson, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 26 days.

(21) Appl. No.: 09/927,097

(22) Filed: Aug. 9, 2001

(65) Prior Publication Data

US 2002/0035328 A1 Mar. 21, 2002

Related U.S. Application Data

(63) Continuation-in-part of application No. 09/663,558, filed on Sep. 15, 2000.
(51) Int. Cl.[7] ................................ A61B 8/00
(52) U.S. Cl. .................................... 600/443
(58) Field of Search ............... 600/443, 447, 600/448, 449, 444, 445, 437; 128/916

(56) References Cited

U.S. PATENT DOCUMENTS

| 4,694,434 A | 9/1987 | von Ramm et al. |
| 5,159,931 A | 11/1992 | Pini |
| 5,229,933 A | 7/1993 | Larson, III |
| 5,454,371 A | 10/1995 | Fenster et al. |
| 5,485,842 A | 1/1996 | Quistgaard |
| 5,522,393 A | 6/1996 | Phillips et al. |
| 5,546,807 A | 8/1996 | Oxaal et al. |
| 5,928,151 A | 7/1999 | Hossack et al. |
| 5,997,479 A | 12/1999 | Savord et al. |
| 6,174,287 B1 * | 1/2001 | Resnick et al. ............ 600/458 |
| 6,179,780 B1 * | 1/2001 | Hossack et al. ............ 600/437 |
| 6,280,387 B1 * | 8/2001 | Deforge et al. ............ 128/916 |
| 6,447,454 B1 * | 9/2002 | Chenal et al. ............ 600/449 |

* cited by examiner

Primary Examiner—Francis J. Jaworski
Assistant Examiner—Maulin Patel
(74) Attorney, Agent, or Firm—W. Brinton Yorks, Jr.

(57) ABSTRACT

An ultrasound system which performs two dimensional imaging is upgradeable to a system which also performs three dimensional ultrasonic imaging. The ultrasound system contains space in which an optional 3D beamformer may be installed to provide the ultrasound system with three dimensional imaging capability. When the 3D beamformer is installed a scanhead select module connects one of a plurality of scanhead connectors to the proper beamformer for the imaging procedure commanded by the user.

21 Claims, 7 Drawing Sheets

DUAL BEAMFORMER ULTRASOUND SYSTEM FOR 2D AND 3D IMAGING

This is a continuation-in-part of U.S. patent application Ser. No. 09/663,558 filed Sep. 15, 2000 and entitled "2D ULTRASONIC TRANSDUCER ARRAY FOR TWO DIMENSIONAL AND THREE DIMENSIONAL IMAGING."

This invention relates to ultrasonic diagnostic imaging systems and, in particular, to ultrasonic diagnostic imaging systems which incorporate both a two dimensional (2D) beamformer and a three dimensional (3D) beamformer.

Until recently the clinical practice of ultrasonic diagnostic imaging has been the province of ultrasound systems which make two dimensional (2D) images of planes scanned by a transducer probe. The performance of such 2D ultrasound imaging systems has continually improved, reaching today's current levels of high image quality and high frame rates of display. The high frame rates provided by current ultrasound systems have enabled virtually any acoustically accessible region of the body to be scanned by real time imaging.

Over the past decade ultrasound designers have begun to address the prospect of producing 3D images rather than 2D images. Initially these efforts have attempted to utilize current 2D scan converters and image processors to produce 3D displays, such as the system described in U.S. Pat. No. 5,485,842. This and other systems in the marketplace would require the user to acquire multiple 2D images from a region of the body, then submit the data to an onboard or offline processor, which would post-process the ultrasound data to produce a 3D display.

With the success of these initial post-processing systems designers have begun to develop real time 3D ultrasound systems, in which the acquired 3D information may be displayed in real time (live as it is acquired). However the initial efforts in this regard are proving to be very expensive, as designers try to provide 3D images with the same image quality as today's 2D images in specially-designed 3D imaging machines. Accordingly it is desirable to provide an affordable means for ultrasound users to move up to 3D capabilities without losing their investments previously made in 2D ultrasound imaging systems.

In accordance with the principles of the present invention, an ultrasound system having a 2D beamformer is upgradeable to 3D imaging capability by the addition of a 3D beamformer. The upgrade may occur at the time of manufacture, for instance, when the customer opts for the optional 3D beamformer, or later in time when the customer desires to upgrade the 2D imaging system to 3D capability. In an illustrated embodiment, the upgrade is performed by adding 3D beamformer integrated circuits or printed circuit boards to the ultrasound system. In the illustrated embodiment the 2D and 3D beamformers share a common controller, which connects scanheads to the appropriate beamformer. Preferably the 2D beamformer exhibits higher performance characteristics, thereby enabling the use of lower-cost components for the 3D beamformer, and allowing the more sensitive diagnostic procedures to be imaged with the greater image quality which is expected of the 2D beamformer.

Figure 1:
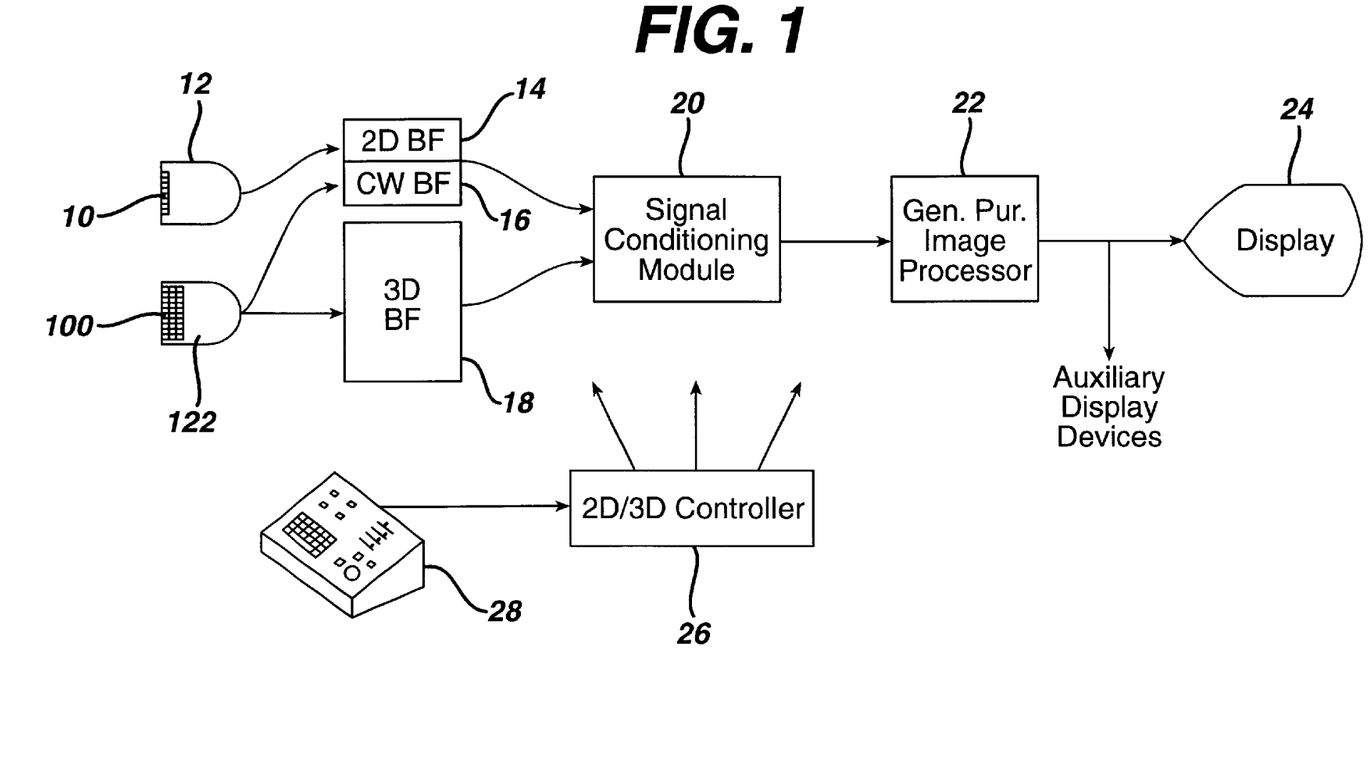
FIG. 1 illustrates in block diagram form a diagnostic ultrasound system constructed in accordance with the principles of the present invention.

Referring first to FIG. 1, an ultrasound system constructed in accordance with the principles of the present invention is shown in block diagram form. The system includes two imaging beamformers, a 2D beamformer 14 and a 3D beamformer 18. The system also includes a CW beamformer 16 which is used to transmit and receive a continuous wave (CW) Doppler signal. The beamformers of the system operate with a one dimensional (1D) array transducer 12 shown with a 1D transducer array 10, or a two dimensional (2D) array transducer 122 shown with a 2D transducer array 100. The beamformers are coupled to a signal conditioning module 20 which processes and conditions the beamformed signals for the particular imaging mode selected by the user, e.g., B-mode, continuous wave, or pulse wave Doppler. The conditioned signals are coupled to a general purpose image processor 22 which forms the desired images. The image data is displayed on a display 24, or coupled to an auxiliary display or printing device such as a stereo display glasses. Overall operation of the system is directed by a 2D/3D controller 26, which controls the ultrasound system as directed by user operation of a user interface 28.

Figure 2:
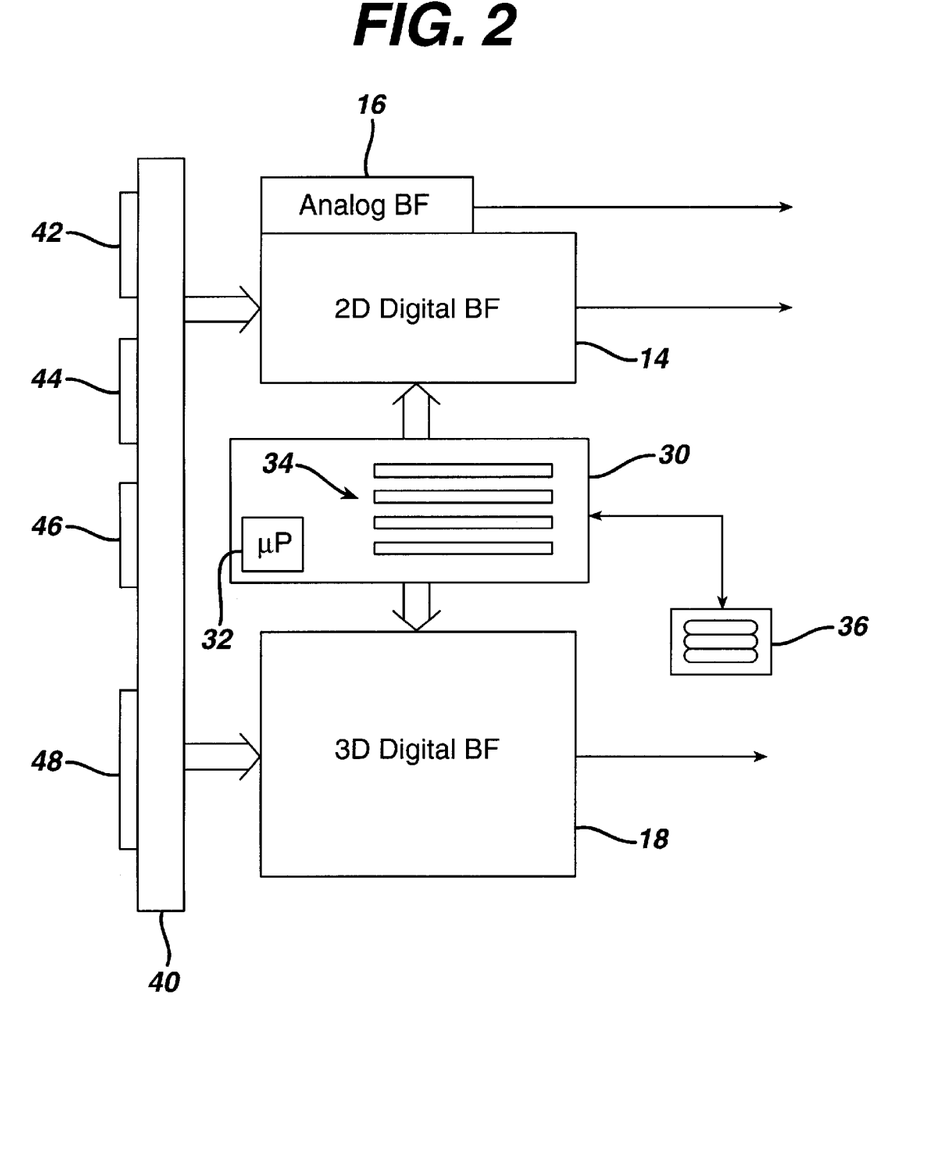
FIG. 2 illustrates the scanhead selection and beamformer arrangement of an embodiment of the present invention.

A more detailed drawing of a beamformer and scanhead select architecture of the present invention is shown in FIG. 2. A scanhead select module 40 includes four scanhead connectors by which scanheads are connected to the system beamformers. Multiple connectors 42, 44, and 46 are provided for simultaneously connecting three different 1D array scanheads to the ultrasound system. These connectors generally mate with scanheads of 64, 128 or more transducer elements A connector 48 is provided for connecting a 2D array scanhead to the ultrasound system. This connector generally mates with a 2D array scanhead of several thousand transducer elements. When the system operator selects a particular scanhead by means of the user interface 28, the scanhead select module routes the signals between the elements of the selected scanhead and the channels of the proper beamformer. This routing may be done by the setting of solid state or mechanical switches, for instance. When a 1D array scanhead is selected for CW Doppler use, for example, the scanhead select module will connect the elements of the selected scanhead to the analog beamformer 16 for analog CW Doppler beamformation. When a 1D array scanhead is selected for 2D imaging, either Doppler, B mode, or a combination thereof, the scanhead select module connects the elements of the selected scanhead to the 2D digital beamformer 14. When a 2D array scanhead is connected to connector 48 and is selected for 2D or 3D imaging, the scanhead select module connects elements of the 2D array scanhead to the 2D digital beamformer 14, the CW beamformer 16, or the 3D digital beamformer 18.

When a scanhead and a beamformer are selected, the selected beamformer is conditioned for the desired type of operation by the beamformer controller 30. In the illustrated embodiment the beamformer controller includes a microprocessor 32 which activates the proper beamformer and programs the beamformer to operate with the proper delays in each channel by use of the delay data stored in scanhead table memory 34. The beamformer controller 30 may access different or additional scanhead delay tables which are stored on a disk drive 36 and may be loaded into the scanhead table memory as needed. The beamformer controller 30 supplies delay data to the analog, 2D digital and 3D digital beamformers when all are installed in the ultrasound system. When one of the beamformers is not currently present or active in the ultrasound system, the beamformer controller provides delay data to the beamformers which are present and selected in the system. The delay tables may be in the form of delay values which are used directly by the beamformers, or in the form of variables for algorithms executed on the beamformer controller or in the beamformers which calculate the appropriate delay values for beamformation.

Figure 3:
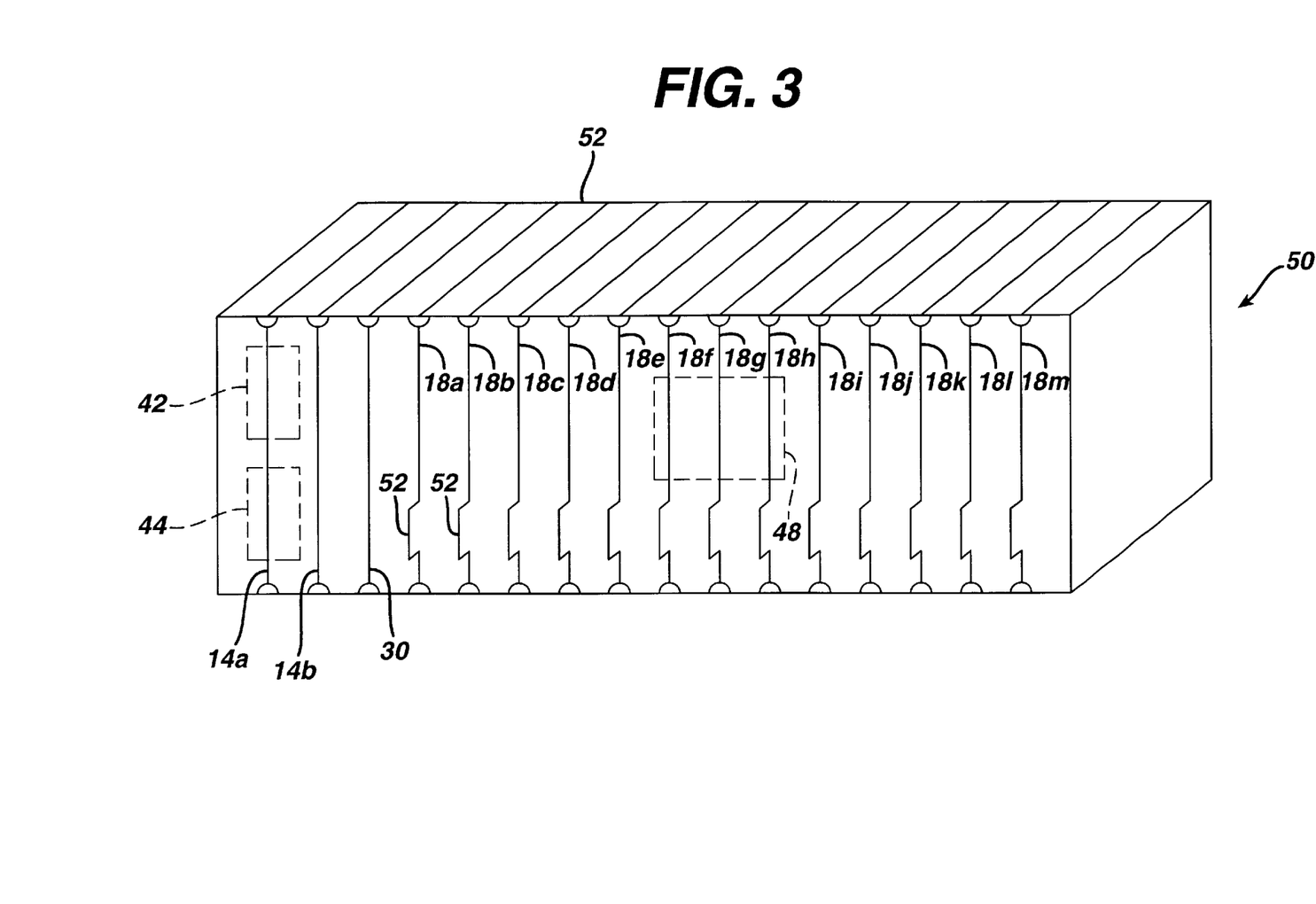
FIG. 3 illustrates a card cage for a dual beamformer ultrasound system.

FIG. 3 illustrates a beamformer card cage for the beamformer printed circuit boards (PCBs) of an embodiment of the present invention. One skilled in the art will recognize that an ultrasound system card cage normally has slots for all the PCBs used by the system, including those of the signal conditioning module and the image processor. However, for ease of illustration, only the PCBs associated with the 2D and 3D beamformers 14 and 18 are shown in the drawing of card cage 50 in FIG. 3. The card cage 50 in the illustrated embodiment has slots for sixteen PCBs labeled 14a through 18 m in the drawing. At the back of the card cage 50 is a backplane 52 having connectors (not visible in this drawing) which engage the remote end of each PCB, and power lines and signal and data buses which connect to the PCBs through the connectors. When the ultrasound system is equipped with only a 2D beamformer only the first three slots of the card cage 50 are occupied. The first and second slots (from left to right) of the card cage are occupied by PCBs 14a and 14b of the 2D digital beamformer 14, and the third slot is occupied by the beamformer controller PCB 30. Shown in phantom at 42 and 44 are representations of the scanhead connectors for 1D array scanheads and scanhead select module which are connected to the 2D beamformer. The scanhead select module is generally in proximity to the scanhead connectors. The scanhead connectors need not be associated with the card cage 50, but are generally located on some other surface where the scanheads can be easily connected, considering such factors as scanhead cable handling and access. The scanhead connectors may be on a lower portion of the ultrasound system below the user interface, or on top of the ultrasound system where the scanheads can be plugged in without requiring the operator to bend over. The scanhead select module can be connected to the card cage backplane or to a PCB by a cable inside the ultrasound system, for instance. In a typical embodiment each 2D beamformer PCB will have 64 channels to control transmission by and process the echo signals from 64 elements of an array transducer. Each of these channels may be capable of multiline processing as described in U.S. patent application Ser. No. 09/746,165 entitled MULTILINE ULTRASOUND BEAMFORMERS and thereby can produce multiple receive beams from a single transmit beam. Thus, the 2D beamformer PCBs 14a and 14b under control of the beamformer controller form a beamformer for a 1D array transducer of up to 128 elements. Additional beamformer PCBs or greater board channel density may be employed to accommodate scanheads with greater numbers of array elements.

An ultrasound system may be manufactured and installed with just the 2D beamformer present. Such a beamformer is preferably of high performance, capable of very good lateral and axial resolution and capable of providing beamformed signals for highly diagnostic and quantitative images. The 2D images it provides will preferably be produced at a relatively high real time frame rate of display. At the time of manufacture or later after the ultrasound system is in service, it may be desirable to upgrade the ultrasound system to a real time 3D imaging capability. In such case 3D beamformer PCBs 18a–18m are installed in the card cage 50. Like the 2D beamformer the PCBs of the 3D beamformer are powered and interconnected from the backplane 52 of the card cage. Preferably the 3D beamformer is controlled by the same beamformer controller 30 as the 2D beamformer, although a separate beamformer controller for the 3D beamformer may also be installed or the beamformer controller for the 2D beamformer may be upgraded to a new controller which controls both beamformers. Shown in phantom in front of the 3D beamformer PCBs 18a–18m is an outline 48 representing the connector and scanhead select module for a 2D array scanhead to be used with the 3D beamformer. This connector and scanhead select module can be grouped with the other 1D array scanhead connectors on the ultrasound system and can share a common scanhead select module, which is preferable for routing signals from the elements of any scanhead to any beamformer, as described below. Alternatively, the 2D array scanhead and scanhead select module can be located on a frontplane panel which mounts on edge connectors 52 on the edges of the 3D beamformer PCBs 18a–18m as shown in FIG. 3. Such an arrangement advantageously reduces the cabling required to connect a 2D array scanhead connector to the 3D beamformer. The frontplane panel can be used to mount and provide scanhead selection for all of the scanhead connectors of the ultrasound system.

Suitable PCBs 18a–18m will generally have higher channel counts than do the PCBs of the 2D beamformer to accommodate the higher elements of a 2D array transducer. Thirteen PCBs 18a–18m with 256 channels each will provide separate channels for 2D arrays of up to 3328 elements. While exhibiting higher channel counts than the PCBs of the 2D beamformer, this increased channel density can be accommodated by relaxing requirements for performance characteristics as compared to the 2D beamformer, such as maximum transducer frequency, number of bits of resolution of A/D converters, transmit waveform shaping, aberration correction, and receive filtering. This will generally be a satisfactory trade-off, as the volume of a 3D region often occupies a volume of a size which may be satisfactorily scanned with a lower frequency transducer, lesser dynamic range and signal-to-noise ratio, and less signal processing than is the case for a high performance 2D beamformer. Furthermore, a broader transmit beam can be used as an advantage in a 3D beamformer by applying it for multiline reception. In addition, since the speed of sound limitations extend the time required to scan a volume significantly over that of a single image plane of the same volume, the 3D data set will often exhibit temporal artifacts, even with the use of multiline 3D acquisition. These limitations allow the requirements for other imaging performance characteristics to be less stringent than those of comparably scaled 2D planar imaging. Reductions in these performance characteristics can also lead to a reduction in the relative cost of the 3D beamformer PCBs, offsetting some or all of the cost of their greater per-board channel count.

Other variations for the 3D beamformer may also be employed. For instance, if the performance of a sparsely populated receive array is acceptable, the channel count of the 3D beamformer can be markedly reduced. For example, four PCBs for a sparse receive 3D beamformer can comprise 128 receive channels each for a total of 512 receive channels for the 2D array beamformer. For transmit it is preferred that a fully populated transmit aperture be used for the most effective steering and focusing performance on transmit. Hence, the four PCBs would include sufficient transmit channels for the largest transmit aperture required by the transducer array. Since transmit channels can be simpler and require less board space than receive channels and transmit apertures are frequently smaller than receive apertures, a smaller number of 3D beamformer PCBs can generally provide the required number of transmit channels in combination with the reduced number of receive channels required for sparse aperture reception.

Figure 4:
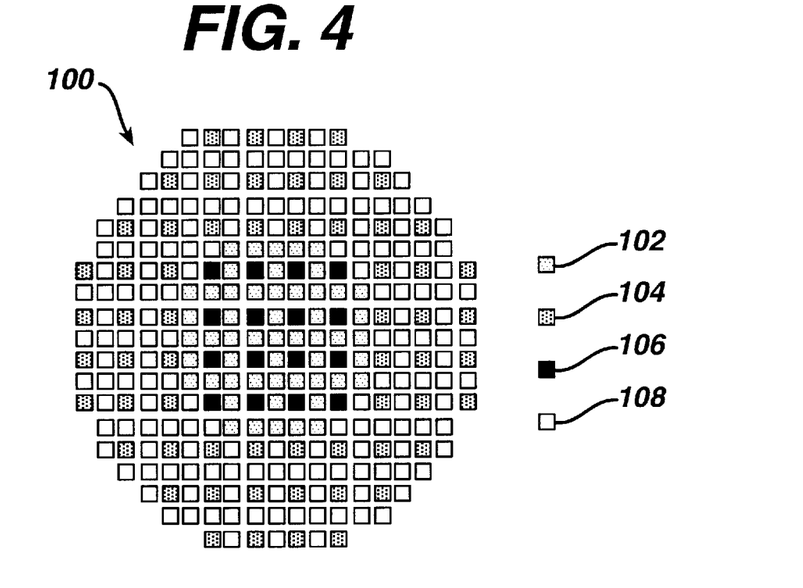
FIG. 4 illustrates a 2D transducer array which utilizes different transmit and receive apertures for 3D imaging.
Figure 5:
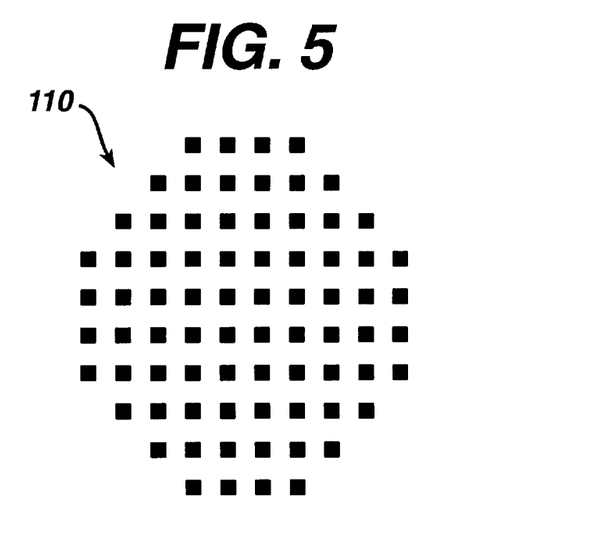
FIG. 5 illustrates a 2D sparse receive aperture of the 2D array of FIG. 4.
Figure 6:
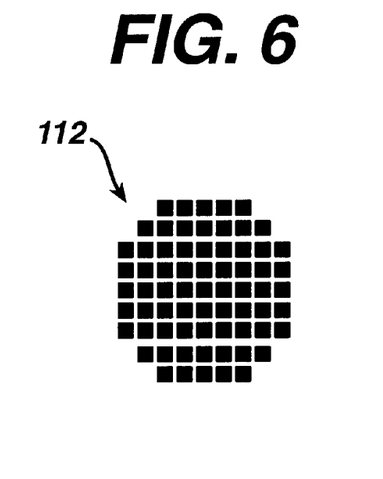
FIG. 6 illustrates a fully populated transmit aperture of the 2D array of FIG. 4.

A transducer array which is ideally suited for a 2D/3D beamformer system is one which can operate with either beamformer to perform either 2D or 3D imaging such as that shown in FIGS. 4–7. The transducer array illustrated in FIGS. 4–7 uses different sets of elements for transmission and reception during the 3D imaging mode: a small, full 2D aperture for transmit and a large, sparse 2D aperture for receive. FIG. 4 illustrates an approximately circular subset of a 19×19 2D array 100 drawn with four types of shading as indicated to the right of the drawing. The lightly shaded elements 102 are used for transmission in the 2D array mode of operation for 3D imaging. The moderately shaded elements 104 are used for reception in the 2D array (3D imaging) mode. The darkly shaded elements 106 are used for both transmission and reception in the 2D array (3D imaging) mode. The unshaded elements 108 are not used in the 2D array (three dimensional imaging) mode. All of the elements are used in the 1D array (two dimensional imaging) mode of operation. As a result, the elements which form the sparse 2D array configuration 110 of FIG. 5, which are elements 104 and 106 of FIG. 4, are used when the array receives echo signals during three dimensional imaging as a sparse 2D array. The elements 112 used to transmit beams for the sparse 2D array mode are shown in FIG. 6, which correspond to elements 102 and 106 of FIG. 4. As the drawings illustrate, beams are transmitted in three dimensions by the small, full 2D transmit aperture of FIG. 6, to generate echoes received by the sparse 2D receive aperture of FIG. 5.

Figure 7:
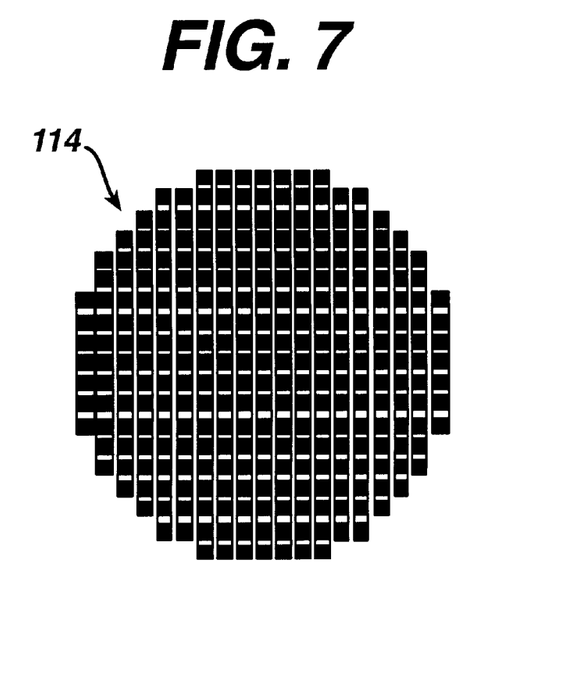
FIG. 7 illustrates the 2D array of FIG. 4 when configured as a 1D array.

In the 1D mode for two dimensional imaging, the elements of the columns are connected together as shown in FIG. 7 to form the full 1D aperture 114.

The 2D array used in FIGS. 4–7 can be a rectangular array as shown in the previous drawings, or can be configured in a shape of more than four sides such as the octagonal shape of FIG. 4. These greater sided polygonal shapes can be advantageous in probes with a circular aperture as they will fill a large percentage of a circular aperture. Since the elements in the 1D array mode shown in FIG. 7 are of unequal lengths and hence exhibit unequal sensitivities, the array will usually be operated with apodization on either transmit or receive or both when used in the 1D mode.

In the embodiments of FIGS. 4–7, a multiplexer is used to switch between 2D transmit, 2D receive, and 1D modes of operation. A multiplexer substantially the same as that described in the parent 09/663,558 application may be used. The elements 108 not used in the 2D (three dimensional imaging) mode are grouped together in columns, with each column connected to a cable through a single-pole single-throw switch as described above. All of the elements 102, 104, 106 used in the 2D sparse array aperture have two switches, one to connect to a cable for 2D-array operation (transmit, receive, or both), and one to connect into a column for 1D operation.

In all of the cases described above it may be desirable to control the electrical boundary condition on the 1D-only elements in 2D mode. This will require only one switch per column.

It will be appreciated that, when sufficient channels are available in either the scanhead or the system beamformer to individually service all of the elements of the full 2D array of FIG. 4, it is preferable to operate the array as a full aperture 2D array on both transmit and receive during 3D imaging.

The transducer array of FIGS. 4–7 is ideally suited for a 2D/3D imaging system because the scanhead select module 40 can switch the elements of the array to the 2D beamformer 14 when the array is configured as shown in FIG. 7 as a 1D array for 2D imaging, and can switch the elements of the array to the 3D beamformer 18 when the array is configured as a 2D array (FIGS. 4–6) for 3D imaging. The system can be time multiplexed to switch both the transducer array and the beamformers between 2D and 3D operation in a time interleaved manner, acquiring 2D image frames with the 2D beamformer 14 which are interspersed during 3D acquisition intervals by the 3D beamformer 18. This mode of operation can be used to present both a 3D image and a 2D image as shown in the display format of FIG. 9 discussed below. It can also be used to intersperse acquisition intervals of spectral Doppler information between intervals of 3D image acquisition.

Figure 8:
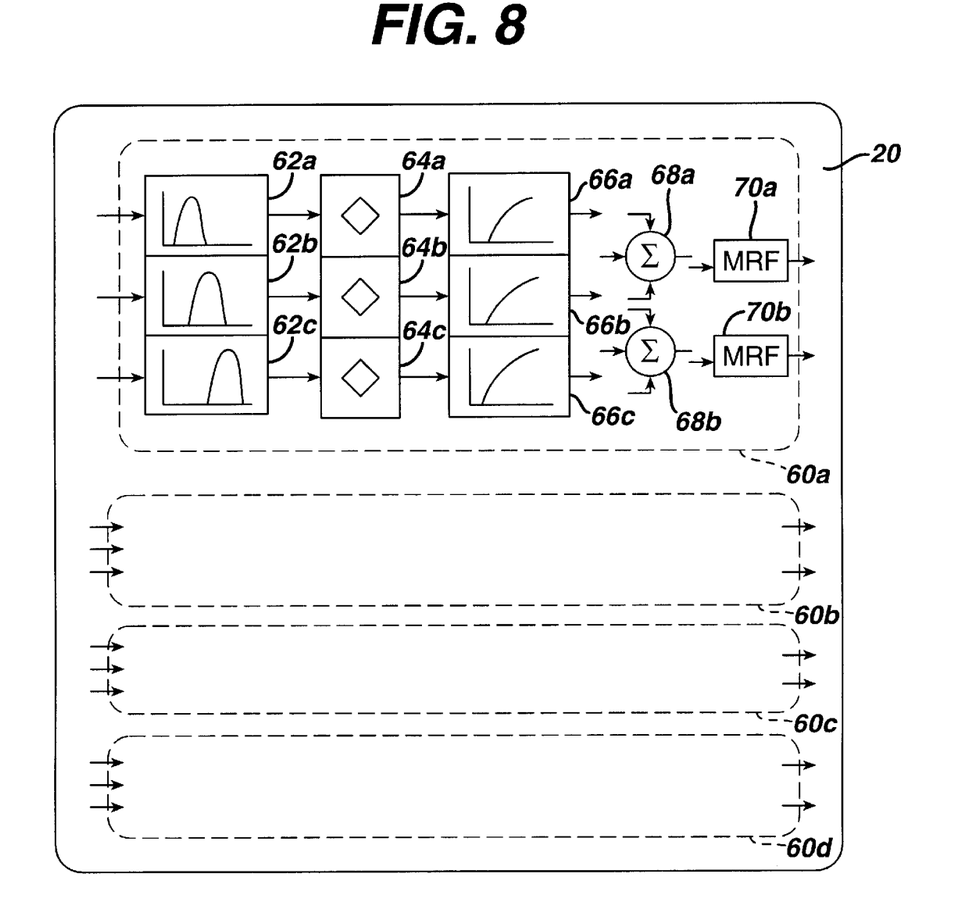
FIG. 8 illustrates a signal conditioning module suitable for use in an ultrasound system constructed in accordance with the principles of the present invention.

FIG. 8 illustrates a signal conditioning module suitable for use in an ultrasound system constructed in accordance with the principles of the present invention. The signal conditioning module 20 illustrated in FIG. 8 is fabricated on a single PCB and contains four identical sections 60a, 60b, 60c, and 60d. The elements of these sections can be combined by multiplexing to form different numbers of processing paths with different performance characteristics, enabling the signal conditioning module to be used with single line beamformers or with high order multiline beamformers often used for 3D imaging. The elements of section 60a are shown in detail. Each section contains three parallel signal paths a, b, and c, with each path containing a bandpass filter (62a; 62b; 62c), a detector (64a; 64b; 64c) and a log compression processor (66a; 66b; 66c). Each bandpass filter may be formed as a quadrature bandpass filter operating as described in U.S. Pat. No. 6,050,942 to produce quadrature signal samples in a programmable passband. The outputs of the quadrature bandpass filters are also selectively coupled to a colorflow and spectral Doppler processor (not shown) which is preferably located on the same PCB as the sections 60a–60b The detectors are used for B mode imaging and the log compression processors scale the signal dynamic range to the characteristics of the display device. With each section containing three such signal paths the illustrated signal conditioning module can filter, detect and log compress up to twelve simultaneously produced B mode multilines at the same time. If a lesser number of lines are being processed simultaneously, other signal processing functions can be provided by multiplexing and combining the outputs of several signal paths. For instance, if only six B mode lines are being processed simultaneously, each beam can be applied to the inputs of two bandpass filters such as bandpass filters 62a and 62b. The passbands of the two filters can be adjusted to be adjacent or only partially overlapping as illustrated in the drawing, separating the beam signal band into two adjacent or slightly overlapping bands. The echo signals used for B-mode imaging can also be Doppler processed through other signal processing paths as described in U.S. Pat. No. 6,139,501. The signals in the two bands are separately detected by detectors 64a and 64b, are log compressed, and then directed by multiplexing to two inputs of a summer 68a. The summer combines the separately detected bands, thereby accomplishing frequency compounding which will reduce the speckle content of the resultant image. The processed signals are applied to a multirate filter 70a, from which they are coupled to the image processor. Each section includes a second summer 68b and a second multirate filter 70b, which by multiplexing can be connected to signal paths in that section in combination with signal paths from other sections of the module. With the signal conditioning module 20 of FIG. 8, six multiline beams can be simultaneously processed in this manner.

As another alternative, four multiline beams can be simultaneously processed by three-band frequency compounding, with each section processing a unique beam. The beam that is applied to section 60a is applied to the three bandpass filters 62a, 62b, and 62c, each of which passes a different sub-band of the received echo signal. The signals in the three bands are detected, log compressed, then combined by summer 68a. The resulting three-band frequency compounding provides better speckle reduction than does the previous example using two-band speckle reduction. The speckle reduced beam is passed through the multirate filter 70a and forwarded for image processing. Each of the other sections 60a, 60b, and 60c processes a different beam in the same manner, which means that the illustrated signal conditioning module can perform three-band frequency compounding on the four beams produced simultaneously by a 4×multiline beamformer. This same concept can be extended to higher order frequency compounding such as use of the signal conditioning module-to perform four-band frequency compounding on three simultaneous beams.

In the final processor of the ultrasound system of FIG. 1 the received and processed beams are used to produce an image in the desired display format. The image processor is preferably a general purpose image processor 22 using a commercially available general purpose processor such as a p.c. motherboard with a microprocessor and RAM. The general purpose processor can be processed to perform 2D scan conversion as described in U.S. Pat. No. 5,940,123 or volume rendering of B mode or Doppler signal data or a combination of the two as described in U.S. Pat. Re. 36,564, U.S. Pat. No. 5,485,842, or U.S. Pat. No. 5,720,291. Alternatively multiplanar reconstruction of a 3D data set can be performed by the general purpose processor as described in U.S. Pat. No. 6,443,896. Thus, the general purpose image processor 22 is capable of producing either 2D or 3D images in a variety of display formats.

Figure 9:
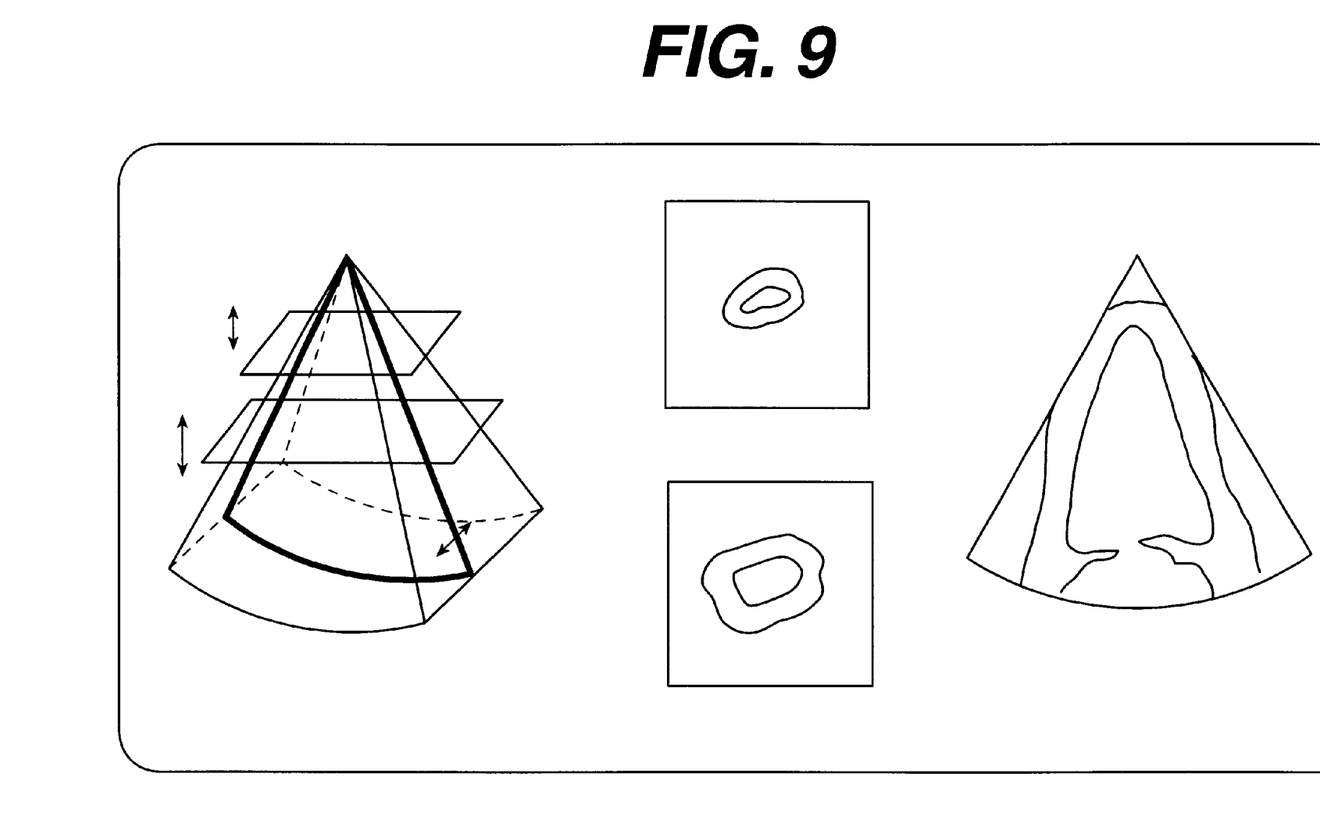
FIG. 9 illustrates a display format for an ultrasound system constructed in accordance with the principles of the present invention.

FIG. 9 illustrates a 3D multiplanar reformatted image display which may be advantageously used to analyze selectable planes of a 3D image. Shown at the left of the display is a real time 3D display of a volumetric region of the body. In the illustrated embodiment the volumetric region is scanned in a 3D phased array format, producing a pyramidal, wedge-shaped volume 80. Intersecting the volume 80 are three adjustable planes 82, 84, and 86 which define the cut planes shown in static or real time in the three image areas on the right side of the display. The two horizontal planes 82 and 84 can be moved up and down through the volumetric region (as indicated by the arrows) by dragging them with a pointing device (or with a finger in the case of a touch screen display) until they intersect horizontal planes of the volume which are to be selectively displayed in images 92 and 94. A third plane 86 pivots from the apex 88 of the volume 80 and can also be dragged by a pointing device (as indicated by the arrow) to delineate a third plane extending from the transducer to the depth of the volume for display in image 96. The volumetric data for the 3D volume display 80 can be processed by the 3D beamformer to produce a 3D image which orients the clinician in the volumetric region, and the planar data for images 92, 94, and 96 can be processed by the 2D beamformer to produce highly diagnostic 2D images of planar regions where accurate, detailed, and precise diagnoses are being performed.

What is claimed is:

1. An ultrasonic diagnostic imaging system comprising:
    an originally installed 2D beamformer; and
    a later installed 3D beamformer,
    wherein a 2D ultrasonic imaging system is upgraded to perform either 2D or 3D imaging.

2. The ultrasonic diagnostic imaging system of claim 1, wherein the 2D beamformer and the 3D beamformer comprise printed circuit boards (PCBs) and further comprising:
    a PCB card cage,
    wherein the PCB card cage has space for one or more 2D beamformer PCBs and for one or more 3D beamformer PCBs.

3. The ultrasonic diagnostic imaging system of claim 2, wherein the PCB card cage has space for a beamformer controller.

4. The ultrasonic diagnostic imaging system of claim 3, wherein the beamformer controller controls at least some of the operations of the 2D beamformer and the 3D beamformer.

5. The ultrasonic diagnostic imaging system of claim 1, wherein the 2D beamformer exhibits higher image quality performance than the 3D beamformer.

6. The ultrasonic diagnostic imaging system of claim 5, wherein the performance of the 2D beamformer is greater than that of the 3D beamformer in one or more of the performance areas of maximum transducer frequency, number of bits of resolution, transmit waveform shaping, aberration correction, and receive filtering.

7. The ultrasonic diagnostic imaging system of claim 1, further comprising:
    a plurality of scanhead connectors; and
    a scanhead select module coupled between the scanhead connectors and the 2D and 3D beamformers.

8. The ultrasonic diagnostic imaging system of claim 7, wherein the scanhead select module acts to operatively connect a selected scanhead connector to a selected one of the beamformers.

9. The ultrasonic diagnostic imaging system of claim 8, wherein one of the scanhead connectors comprises a 2D array scanhead connector; and
    wherein the scanhead select module is operative to connect the 2D array scanhead connector to either the 3D beamformer or the 2D beamformer.

10. The ultrasonic diagnostic imaging system of claim 9, further comprising a 2D array transducer having a probe connector which mates with the 2D array scanhead connector and operable for either 2D imaging or 3D imaging,
    wherein the scanhead select module is operative to connect the 2D array scanhead connector to the 3D beamformer when the 2D array transducer is operative for 3D imaging, and to connect the 2D array scanhead connector to the 2D beamformer when the 2D array transducer is operative for 2D imaging.

11. The ultrasonic diagnostic imaging system of claim 1, wherein the 3D beamformer comprises a multiline beamformer.

12. An ultrasonic diagnostic imaging system comprising:
a 3D beamformer;
a 2D beamformer operable independently from the 3D beamformer;
a beamformer controller;
a signal conditioning processor coupled to the 3D beamformer and the 2D beamformer;
an image processor coupled to the signal conditioning processor; and
a display coupled to the image processor.

13. The ultrasonic diagnostic imaging system of claim 12, wherein the beamformer controller is coupled to the 2D beamformer and the 3D beamformer and is operable to control either beamformer.

14. The ultrasonic diagnostic imaging system of claim 12, wherein the 2D beamformer has m beamformer channels, the 3D beamformer has n beamformer channels which are different from the m beamformer channels, and n is greater than m.

15. The ultrasonic diagnostic imaging system of claim 14, wherein the signal conditioning processor comprises a detector.

16. The ultrasonic diagnostic imaging system of claim 15, wherein the 3D beamformer comprises a multiline beamformer, and wherein the signal conditioning processor comprises a plurality of detectors.

17. The ultrasonic diagnostic imaging system of claim 16, wherein the signal conditioning processor further comprises a frequency compounding processor.

18. The ultrasonic diagnostic imaging system of claim 12, further comprising:
a plurality of scanhead connectors; and
a scanhead select module coupled between the scanhead connectors and the 2D and 3D beamformers.

19. The ultrasonic diagnostic imaging system of claim 18, wherein the scanhead select module acts to operatively connect a selected scanhead connector to a selected one of the beamformers.

20. The ultrasonic diagnostic imaging system of claim 12, wherein the beamformer controller acts to provide delay variables to the 3D beamformer for operation of the imaging system in the 3D imaging mode, and acts to provide delay variables to the 2D beamformer for operation of the imaging system in the 2D imaging mode.

21. The ultrasonic diagnostic imaging system of claim 20, wherein each beamformer acts to calculate delay values using delay variables supplied by the beamformer controller.

* * * * *